United States Patent [19]
Oxford et al.

[11] Patent Number: 5,066,660
[45] Date of Patent: Nov. 19, 1991

[54] INDOLE DERIVATIVES

[75] Inventors: Alexander W. Oxford; Ian H. Coates, both of Hertford; Darko Butina, Bedfordshire, all of England

[73] Assignee: Glaxo Group Limited, London, England

[21] Appl. No.: 570,513

[22] Filed: Aug. 21, 1990

Related U.S. Application Data

[63] Continuation of Ser. No. 231,260, Aug. 12, 1988, abandoned.

[30] Foreign Application Priority Data

Aug. 13, 1987 [GB] United Kingdom ............... 8719167

[51] Int. Cl.$^5$ ................. C07D 401/04; A61K 31/445
[52] U.S. Cl. .................................. 514/323; 514/339; 546/201; 546/273
[58] Field of Search ............... 546/201, 273; 514/323, 514/339

[56] References Cited

U.S. PATENT DOCUMENTS

| | | | |
|---|---|---|---|
| 4,278,677 | 7/1981 | Nedelec et al. | 546/273 X |
| 4,530,932 | 7/1985 | Clemence et al. | 514/318 |
| 4,548,939 | 10/1985 | Kennis et al. | 514/265 |
| 4,711,893 | 12/1987 | Hausberg et al. | 514/339 |
| 4,808,581 | 2/1989 | Oxford et al. | 546/201 X |

FOREIGN PATENT DOCUMENTS

| | | |
|---|---|---|
| 0147107 | 7/1985 | European Pat. Off. |
| 0200322 | 11/1986 | European Pat. Off. |
| 1556919 | 11/1979 | United Kingdom |
| 2035310 | 6/1980 | United Kingdom |
| 2124210 | 2/1984 | United Kingdom |
| 2150932 | 7/1985 | United Kingdom |
| 2162522 | 2/1986 | United Kingdom |
| 2168347 | 6/1986 | United Kingdom |
| 2168973 | 7/1986 | United Kingdom |

OTHER PUBLICATIONS

J. Guillaume et al., *Eur. J. Med. Chem.*, 22, 1987, 33–43.
S. Peroutka et al., *J. Pharm. Exp. Ther.*, 237 (3), 901–906 (1986).
E. Taylor et al., *J. Pharm. Exp. Ther.*, 236 (1), 118–125 (1986).

*Primary Examiner*—Jane T. Fan
*Attorney, Agent, or Firm*—Bacon & Thomas

[57] ABSTRACT

Compounds are disclosed of formula (I)

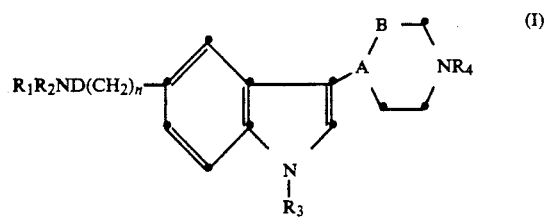

wherein
$R_1$ represents H or $C_{1-6}$ alkyl;
$R_2$ represents H, $C_{1-6}$ alkyl, $C_{3-7}$ cycloalkyl, $C_{3-6}$ alkenyl, phenyl or phen($C_{1-3}$)alkyl in which the phenyl ring is optionally substituted by halogen, $C_{1-4}$ alkoxy, hydroxy or $C_{1-3}$ alkyl;
$R_3$ represents H, $C_{1-3}$ alkyl, —$CO_2R_5$, —$COR_5$, —$COCO_2R_5$ or —$CONHR_5$ where
$R_5$ represents H, $C_{1-4}$ alkyl, $C_{3-7}$ cycloalkyl, $C_{2-4}$ alkenyl, aryl or ar($C_{1-4}$)alkyl in which the aryl group is optionally substituted by halogen, $C_{1-4}$ alkoxy, $C_{1-4}$ alkyl or hydroxy) (provided that where $R_3$ represents —$CO_2R_5$, $R_5$ is other than H);
$R_4$ represents H, $C_{1-3}$ alkyl, $C_{3-6}$ alkenyl, phenyl or phen($C_{1-3}$)alkyl;
A–B represents CH—$CH_2$—or C=CH—
D represents —CO— or —$SO_2$—
n represents 0, 1–5;

provided that when D represents —$SO_2$, n is 2, $R_3$ represents H and $R_4$ represents H or $C_{1-3}$ alkyl, $R_2$ is other than H or $C_{1-6}$ alkyl; and pharmaceutically acceptable salts and solvates (for example hydrates) thereof.

The compounds are indicated as useful for the treatment of migraine, cluster headache, chronic paroxysmal hemicrania and headache associated with vascular disorders.

Processes and intermediates for their preparation and pharmaceutical compositions containing them are also disclosed.

25 Claims, No Drawings

INDOLE DERIVATIVES

This application is a continuation of application Ser. No. 07/231,260, filed Aug. 12, 1988, now abandoned.

This invention relates to indole derivatives, to processes for their preparation, to pharmaceutical compositions containing them and to their medical use, in particular to compounds and compositions of use in the treatment of migraine.

It has been suggested that the pain of migraine may be associated with excessive dilatation of the cranial vasculature and known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic usually in combination with an entimetic but such treatments are of limited value.

More recently, indole derivatives which are selective 5HT$_1$-like receptor agonists and which exhibit selective vasoconstrictor activity have been described in the art as useful in the treatment of migraine (see for example A.-Doenicke, J.-Brand, V. L. Perrin, Lancet, 1988, 1309–1311).

We have not found a novel group of indole derivatives which exhibit 5HT$_1$-like receptor agonist activity and selective vasoconstrictor activity.

Thus, the present invention provides an indole of formula (I):

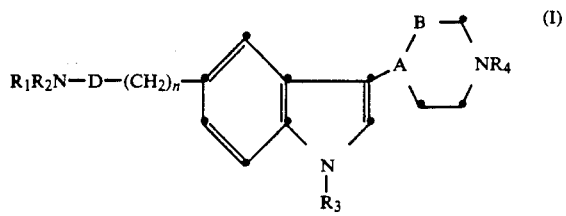

wherein
$R_1$ represents a hydrogen atom or a $C_{1-6}$ alkyl group;
$R_2$ represents a hydrogen atom, a $C_{1-6}$ alkyl group, a $C_{3-7}$ cycloalkyl group, a $C_{3-6}$ alkenyl group, or a phenyl or phen($C_{1-3}$)alkyl group in which the phenyl ring is optionally substituted by a halogen atom, a $C_{1-4}$ alkoxy group, a hydroxy group or a $C_{1-3}$ alkyl group;
$R_3$ represents a hydrogen atom, a $C_{1-3}$ alkyl group or a group —CO$_2$R$_5$, —COR$_5$, —COCO$_2$R$_5$ or —CONHR$_5$ where R$_5$ represents a hydrogen atom, a $C_{1-4}$ alkyl group, a $C_{3-7}$ cycloalkyl group, a $C_{2-4}$ alkenyl group or an aryl or ar($C_{1-4}$)alkyl group in which the aryl group may be unsubstituted or substituted by a halogen atom, a $C_{1-4}$ alkoxy group, a $C_{1-4}$ alkyl group or a hydroxy group (provided that when R$_3$ represents —CO$_2$R$_5$, R$_5$ is other than hydrogen);
$R_4$ represents a hydrogen atom, a $C_{1-3}$ alkyl group, a $C_{3-6}$ alkenyl group, a phenyl group or a phen($C_{1-3}$)alkyl group;
A—B represents the group CH—CH$_2$— or C=CH—;
D represents the group —CO— or —SO$_2$—;
n represents zero or an integer from 1 to 5;
and pharmaceutically acceptable salts or solvates (for example hydrates) thereof provided that when D represents the group —SO$_2$—, n is 2, R$_3$ is hydrogen and R$_4$ is hydrogen or $C_{1-3}$ alkyl, then R$_2$ is other than hydrogen or $C_{1-6}$ alkyl.

Referring to the general formula (I), an alkyl group either as such or as part of an alkoxy or phenalkyl group may be a straight chain or branched chain alkyl group such as a methyl, ethyl or prop-2-yl group.

A $C_{3-7}$ cycloalkyl group may be a cyclopropyl, cyclobutyl, cyclopentyl, cyclohexykl or cycloheptyl group.

A $C_{3-6}$ alkenyl group may be, for example, a propenyl, 2-propenyl or butenyl group. Where R$_2$ and/or R$_4$ represents an alkenyl group, it will be appreciated that the double bond may not be adjacent to the nitrogen atom.

When R$_2$ represents a substituted or unsubstituted phen($C_{1-3}$)alkyl group, the alkyl moiety of the group is preferably a methyl or ethyl moiety.

A halogen substituted in the compounds of general formula (I) may be a fluorine, chlorine, bromine or iodine atom. A $C_{1-4}$ alkoxy group may be, for example, a methoxy or ethoxy group.

An aryl group, either as such or as part of an ar($C_{1-4}$)alkyl group is preferably phenyl.

In one preferred class of compounds represented by formula (I), D represents the group —SO$_2$—.

In another preferred class of compounds of formula (I), D represents the group —CO—.

Another preferred class of compounds of formula (I) is that in which A—B represents the group —CH—CH$_2$—.

In the compounds of formula (I), R$_1$ preferably represents a hydrogen atom or a $C_{1-3}$ alkyl group such as methyl.

R$_2$ in the compounds of formula (I) preferably represents a hydrogen atom or a $C_{1-3}$ alkyl group such as methyl. In an alternative preference, R$_2$ represents a phen($C_{1-3}$)alkyl group such as phenethyl.

Conveniently R$_1$ and R$_2$ when considered together comprise from 1 to 3 carbon atoms. Obviously when R$_1$ and R$_2$ comprise an alkyl group containing one carbon atom, then one of R$_1$ or R$_2$ is hydrogen.

In the compounds of formula (I), R$_3$ may be, for example, a methyl group but is preferably a hydrogen atom.

The substituent R$_4$ is preferably a $C_{1-3}$ alkyl group such as methyl.

n preferably represents 0, 1 or 2.

An alternative preferred class of compounds within the scope of formula (I) has the formula (Ia)

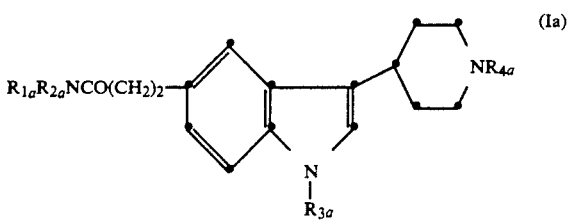

wherein
$R_{1a}$ represents a hydrogen atom or a $C_{1-6}$ (preferably $C_{1-3}$) alkyl group;
$R_{2a}$ represents a hydrogen atom or a $C_{1-6}$ (preferably $C_{1-3}$)alkyl group;
$R_{3a}$ represents a hydrogen atom or a $C_{1-3}$ alkyl group;
$R_{4a}$ represents a hydrogen atom or a $C_{1-3}$ alkyl group;
and pharmaceutically acceptable salts and solvates (for example hydrates) thereof.

Suitable pharmaceutically acceptable salts are those conventionally known in the art. Examples of physiologically acceptable salts include acid addition salts formed with inorganic acids, such as hydrochlorides, hydrobromides, phosphates and sulphates, and with organic acids, for example tartrates, maleates, fumarates, succinates and sulphonates. Other salts which are not pharmaceutically acceptable may be useful in the preparation of compounds of formula (I) and these form a further part of the invention.

The invention embraces all optical isomers of the compounds of formula (I) and their mixtures, including racemic mixtures thereof. The invention also includes within its scope all geometric isomers of the compounds of formula (I).

The selective $5HT_1$-like receptor agonist activity and selective vasoconstrictor activity of the compounds of the invention have been demonstrated in vitro. In addition, certain of the compounds of the invention have been found to selectively constrict the carotid arterial bed of the anaesthetised dog whilst having negligible effect on blood pressure.

Compounds of the invention are useful in treating conditions associated with cephalic pain. In particular, the compounds are useful in the treatment of migraine, cluster headache, chronic paroxysmal hemicrania and headache associated with vascular disorders and in alleviating the symptoms associated therewith.

Accordingly, the invention also provides a pharmaceutical composition which comprises at least one compound of formula (I) or a pharmaceutically acceptable salt or solvate (e.g. hydrate) thereof and formulated for administration by any convenient route. Such compositions are preferably in a form adapted for use in medicine, in particular human medicine, and can conveniently be formulated in conventional manner using one or more pharmaceutically acceptable carriers or excipients.

In a further aspect there is provided a compound of formula (I) or a salt or solvate thereof for use in therapy, in particular in human medicine. It will be appreciated that use in therapy embraces but is not necessarily limited to use of a compound of formula (I) or a salt or solvate thereof as an active therapeutic substance.

There is also provided as a further aspect of the invention the use of a compound of formula (I) in the preparation of a medicament for use in the treatment of conditions associated with cephalic pain, in particular migraine, cluster headache, chronic paroxysmal hemicrania and headache associated with vascular disorders.

In an alternative or further aspect there is provided a method for the treatment of a mammal, including man, comprising administration of an effective amount of a compound of formula (I) or salt or solvate thereof in particular in the treatment of conditions associated with cephalic pain.

It will be appreciated that reference to treatment is intended to include prophylaxis as well as the alleviation of established symptoms. Compounds according to the invention may be administered as the raw chemical but the active ingredient is preferably presented as a pharmaceutical formulation.

The active ingredient may conveniently be presented in unit dose form. A convenient unit dose formulation contains the active ingredient compound in an amount of from 0.1 mg to 100 mg.

The compounds according to the invention may for example be formulated for oral, sub-lingual buccal, parenteral, rectal or intranasal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

Tablets for sub-lnigual administration may be formulated in a similar manner.

For intranasal administration the compounds of the invention may be used, for example, as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

It will be appreciated that the precise administered will depend on the age and condition of the patient, the particular compound used and the frequency and route of administration. The compound may be administered in single or divided doses and may be administered one or more times, for example 1 to 4 times per day.

A proposed dose of the compounds of the invention for oral, sub-lingual parenteral, buccal, rectal or intranasal administration to man (of approximately 70 kg bodyweight) for the treatment of migraine is 0.1 to 100 mg of the active ingredient per unit does which could be administered, for example, 1 to 4 l times per day.

For oral administration a unit does will preferably contain from 2 to 50 mg of the active ingredient. A unit dose for parenteral administration will preferably contain 0.2 to 5 mg of the active ingredient.

Aerosol formulations are preferably arranged so that each metered dose or 'puff' delivered from a pressurised aerosol contains 0.2 mg to 2 mg of a compound of the invention, and capsules and cartridges delivered from an insufflator or an inhaler, contain 0.2 mg to 20 mg of a compound of the invention. The overall daily dose by inhalation with an aerosol will be within the range 1 mg to 100 mg. Administration may be several times daily, for example from 2 to 8 times, giving for example 1, 2 or 3 doses each time.

Dosages of the compounds of the invention for rectal, sub-lingual or intranasal administration are similar to those for oral administration.

The compounds of the invention may, if desired, be administered in combination with one or more other therapeutic agents, such as analgesics, anti-inflammatory agents and anti-nauseants, and formulated for administration by any convenient route in conventional manner. Appropriate doses will be readily appreciated by those skilled in the art.

According to another aspect of the invention, compounds of general formula (I) and physiologically acceptable salts and solvents (e.g. hydrates) thereof, may be prepared by the general methods outlined below. In the following processes, $R_1$, $R_2$, $R_3$ and $R_4$, the group A—B, the group D, and n are as defined for the general formula (I) unless otherwise specified.

According to one general process (A), compounds of formula (I) wherein A—B is the group C=CH may be prepared by condensing a compound of formula (II):

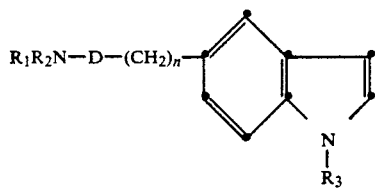

(II)

or a protected or activated derivative thereof, with a piperidone of formula (III):

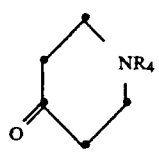

(III)

or a salt or protected derivative thereof.

The condensation reaction may be effected in a suitable reaction medium in the presence of an acid or a base, conveniently at a temperature of 25° to 120° C.

Acids which may be employed in the above process include organic and inorganic acids such as sulphonic acids (e.g. p-toluenesulphonic acid), carboxylic acids (e.g. acetic acid) and preferably strong inorganic acids such as polyphosphoric acid, sulphuric acid and hydrochloric acid. Suitable solvents for the reaction include inert solvents such as ethers (e.g. tetrahydrofuran or dioxan), alcohols (e.g. ethanol) and chlorinated hydrocarbons (e.g. chloroform or carbon tetrachloride). In some cases the acid may also act as the reaction solvent.

It will be appreciated that in order for the above process to be effected in the presence of a base, $R^3$ should represent a hydrogen atom.

Bases which may be employed in the above process include alkali metal hydroxides (e.g. potassium hydroxide), alkali metal alkoxides (e.g. sodium or potassium methoxide, ethoxide or t-butoxide), alkali metal hydrides (e.g. sodium hydride) and alkali metal amides (e.g. sodamide). Suitable solvents for the reaction include alcohols (e.g. methanol or ethanol) ethers (e.g. tetrahydrofuran or dioxan) and dimethylsulphoxide.

Intermediates of formula (II) may be prepared by conventional methods for example by reacting an amine of formula $R_1R_2NH$ with the 3-unsubstituted analogues of compounds of formula (IV) (as described hereinafter) using the methods described for process (B) hereinafter.

According to another general process (B), a compound of formula (I) may also be prepared by condensing an amine of formula $R_1R_2NH$ with an acid of general formula (IV).

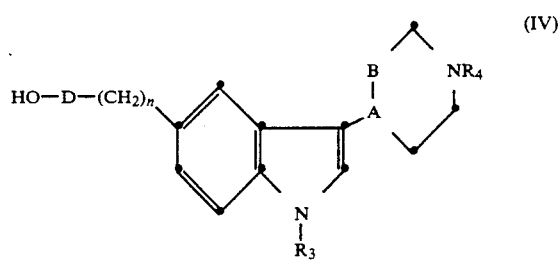

(IV)

or an acylating agent corresponding thereto, or a salt (for example, an organic or inorganic acid addition salt such as the hydrochloride, hydrobromide, maleate, sulphate or creatinine sulphate adduct) or a protected derivative thereof.

Acylating agents corresponding to the acid of general formula (IV) which may conveniently be used in the above process include acid halides (for example carboxylic acid chlorides and sulphonyl chlorides), alkyl esters (for example the methyl or ethyl esters), activated esters (for example, the 2-(1-methylpyridinyl)ester), mixed anhydrides (for example, diphenylcarbamic anhydride or pivalic anhydride), or other activated carboxylic acid derivatives such as those conveniently used in peptide synthesis.

The condensation process involving the acylating agents may be effected in a suitable reaction medium which may be aqueous or non-aqueous and conveniently at a temperature of from −70° to +150° C. Thus the condensation reaction using an acid halide, anhydride or activated ester may be effected in a suitable reaction medium such as an amide (e.g., N,N'-dimethylformamide), an ether (e.g. tetrahydrofuran), a nitrile (e.g. acetonitrile), a haloalkane (e.g. dichloromethane) or mixtures thereof, optionally in the presence of a base such as pyridine or triethylamine or an inorganic base as calcium carbonate or sodium bicarbonate.

The condensation reaction using an alkyl ester may be effected in a suitable reaction medium such as an alcohol (e.g. methanol), an amide (e.g. dimethylformamide), an ether (e.g. tetrahydrofuran) or mixtures thereof and conveniently at a temperature of from 0° to 100° C. In some instances, the amine $R_1R_2NH$ may itself act as reaction solvent.

The reaction involving condensation of an amine $R_1R_2NH$ with a carboxylic acid of general formula (IV) is desirably conducted in the presence of a coupling agent such as carbonyl dimidazole or N,N'-dicyclohexylcarbodiimide. The condensation reaction may be carried out in a suitable reaction medium such as an ether (for example, tetrahydrofuran), a haloalkane (for example, dicloromethane), a nitrile (for example, acetonitrile) or an amide (for example, dimethylformamide) conveniently at a temperature of from −5° to +30° C. The reaction may also be carried out in the absence of a coupling agent in a suitable reaction medium such as a hydrocarbon (for example, toluene or xylene) conveniently at a temperature of from 50° to 120° C.

Where it is desired to prepare a compound of formula (I) in which $R_1$ and $R_2$ are both hydrogen atoms, ammonia may be used in the form of aqueous ammonia or in a solvent such as methanol.

Compounds of formula (IV) and acylating agents corresponding thereto, such as the alkyl esters, are novel and as such constitute a further feature of the invention. Compounds of formula (IV) or acylating agents corresponding thereto may be prepared by methods analogous to those described in UK Patent Specification 2035210 and 'A Chemistry of Heterocyclic compounds—Indles Part II', Chapter VI, edited by W. J. Houlihan (1972) Wiley Interscience, New York or by processes, such as process (A), as described herein.

According to another general process (C), compounds of formula (I) may be prepared by cyclisation of a compound of formula (V)

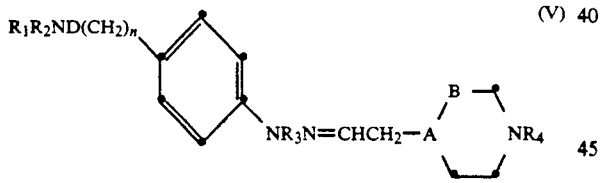

(V)

The process is desirably carried out in the presence of polyphosphate ester in a reaction medium which may comprise one or more organic solvents, preferably halogenated hydrocarbons such as chloroform, dichlormethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in aqueous or non-aqueous media, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be for example an inorganic acid such as concentrated hydrochlorid, polyphosphoric or sulphuric acid. (In some cases the acid catalyst may also act as the reaction solvent). In an anhydrous reaction medium, which may comprise one or more alcohols or ethers (e.g. as described above) or esters (e.g. ethyl acetate), the acid catalyst will generally be a Lewis acid such as boron trifluoride or zinc or magnesium chloride. The cyclisation reaction may conveniently be carried out at temperatures of from 20° to 200° C. preferably 50° to 125° C.

According to a particular embodiment of this process, compounds of general formula (I) may be prepared directly by the reaction of a compound of general formula (VI):

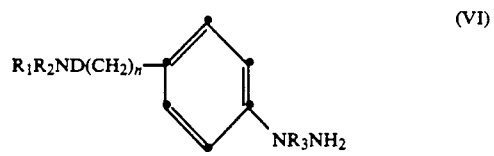

(VI)

or a salt thereof, with a compound of formula (VII):

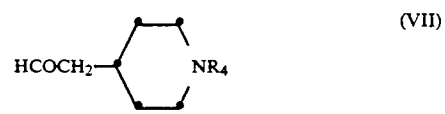

(VII)

or a salt or protected derivative thereof (such as an acetal e.g. formed with an appropriate alkylorthoformate), using the appropriate conditions as described above. It will be appreciated that in this embodiment a compound of formula (V) is formed as an intermediate and may be reacted in situ to form the desired compound of formula (I).

Compounds of the general formula (V) may be isolated as intermediates during the process for the preparation of compounds of general formula (I) wherein a compound of formula (VI), or a salt thereof, is reacted with a compound of formula (VII) or a salt or protected derivative thereof, in a suitable solvent such as an aqueous alcohol (e.g. methanol) and at a temperature of, for example, from 20° to 100° C. If an acetal of a compound of formula (VII) is used it may be necessary to carry out the reaction in the presence of an acid (for example, acetic or hydrochloric acid). In some cases the acid may also act as the reaction solvent.

Compounds of general formula (VI) may be prepared in a number of conventional steps from compounds of formula (VIII)

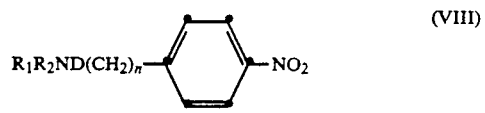

(VIII)

For example, a compound of formula (VIII) may be reduced by catalytic dehydrogenation using a catalyst such as palladium on charcoal to give an amine which may be diazotised using, for example nitrous acid. The product of this reaction may then be reduced using, for example, stannous chloride, to give a compound of formula (VI).

According to another general process (D), a compound of formula (I) wherein n represents 2 to 5 may be prepared by reduction of a compound of formula (IX)

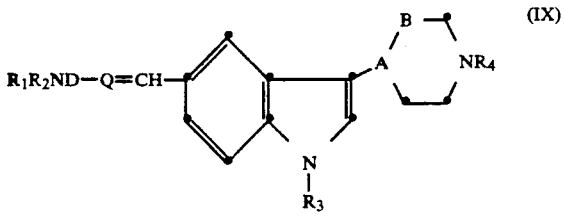

(wherein —Q=CH represents a $C_{2-5}$ alkenyl chain).

The reduction may be effected using similar reaction conditions to those described for general process (A) above.

Compounds of formula (IX) are themselves novel and form a further feature of the invention.

Compounds of formula (IX) may be prepared by condensing a compound of formula (X)

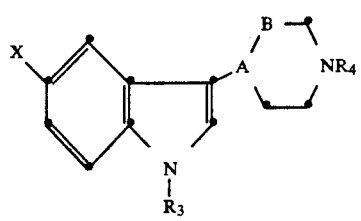

(wherein X represents a leaving atom or group such as a halogen atom for example a bromine atom) with an alkene $R_1R_2NDQ=CH_2$.

The reaction will generally be effected in the presence of a palladium catalyst and a base. The catalyst may be, for example, palladium on charcoal or a palladium salt. Palladium salts which may be employed as catalysts include salts of organic acids such as acetates or salts of inorganic acids such as chlorides or bromides. The base may be, for example, a tertiary nitrogen base such as triethylamine or tri-n-butylamine or an alkali metal carbonate such as sodium carbonate. The reaction may optionally be carried out in the presence of a phosphine, for example a triarylphosphine such as triphenylphosphine or tri-o-tolylphosphine. A phosphine should be present when the process is effected with a compound of formula (XI) wherein X represents a bromine atom.

General process (D) may be effected in the presence or absence of solvent. An anhydrous or aqueous reaction medium comprising one or more solvents may be employed. Suitable solvents include nitriles, for example, acetonitrile, alcohols, for example methanol, amides, for example dimethylformamide, N-methylpyrrolidine or hexamethylphosphoramide; and water. The reaction may conveniently be carried out at a temperature of from 25° to 200° C., preferably 75° to 150° C.

Compounds of formula (X) may be prepared from known compounds by methods analgous to those described herein.

According to another general process (E) a compound of formula (I) according to the invention may be converted into another compound of the invention using conventional procedures.

For example, compounds of formula (I) wherein A—B is the group —CH—$CH_2$— may be prepared by reduction of the corresponding compounds of formula (I) wherein A—B is the group —CH=CH—. The reduction process may conveniently be carried out in the presence of hydrogen and a noble metal catalyst, such as palladium, Raney nickel, platinum, platinum oxide or rhodium which may be supported, for example, on charcoal. Alternatively a homogenous catalyst such as tris(triphenylphosphine) rhodium chloride may be used. The reduction may be carried out in a solvent such as an alcohol e.g. methanol or ethanol, an ether e.g. dioxan, an ester e.g. ethyl acetate or an amide e.g. dimethylformamide and conveniently at a temperature of from −10° to +50° C.

It should be noted however, that the conditions for the reduction of the group A—B when it represents —C=CH—, to the group —CH—$CH_2$, may also effect cleavage of any benzyl groups present or reduction of any other alkenyl group present to an alkyl group.

According to one embodiment of this process, a compound of general formula (I) where A—B represents —CH$CH_2$— and $R_4$ is a hydrogen atom, may be prepared by reduction of a corresponding compound of general formula (I) wherein $R_4$ is a benzyl group, for example with hydrogen in the presence of a catalyst e.g. 10% palladium on charcoal.

According to a further embodiment, a compound of general formula (I) where A—B represents —CH$CH_2$— and $R_2$ represents a $C_{3-6}$ alkyl group may be prepared by reduction of the corresponding compound of formula (I) wherein A—B represents C=CH or —CH$CH_2$— and $R_2$ represents a $C_{3-6}$ alkenyl group. The reduction process may be effected using the conditions as described above for the reduction of the group A—B.

According to another embodiment of general process (E), a compound of formula (I) wherein one or more of $R_1$, $R_2$, $R_3$ and $R_4$ represent hydrogen atoms may be alkylated using conventional techniques. It will be understood that the term 'alkylation' embraces the introduction of an alkyl, cycloalkyl alkenyl or phenylalkyl group. The reaction may be effected using a suitable alkylating agent such as an alkyl halide, alkyl tosylate or dialkylsulphate. The alkylation reaction may conveniently be carried out in an inert organic solvent such as an amide (e.g. dimethylformamide) or an ether (e.g. tetrahydrofuran) preferably in the presence of a base. Suitable bases include, for example, alkali metal hydrides, such as sodium hydride, alkali metal carbonates, such as sodium carbonate or alkali metal alkoxides such as sodium or potassium methoxide, ethoxide or t-butoxide. The alkylation reaction is conveniently carried out at a temperature of from 25° to 100° C.

According to a still further embodiment, a compound of general formula (I) in which $R_3$ represents a group —$CO_2R_5$, —$COR_5$, —$COCOR_5$ or —C ONH$R_5$ may be prepared by acylating the corresponding compound of formula (I) wherein $R_3$ represents a hydrogen atom, or a protected derivative thereof. Acylating agents corresponding to the group $R^3$ which may be used in this general process include acid halides (e.g. acid chlorides such as acetyl chloride); alkyl haloformates (e.g. methyl or ethyl chloro- formate); mixed or symmetrical anhydrides (e.g. acetic anhydride or benzoic anhydride); carbonates (e.g. diethyl carbonate); and isocyanates (e.g. methyl isocyanate).

The reaction is conveniently effected in the presence of a base, such as an alkali metal hydride, e.g. sodium or potassium hydride; an alkali metal carbonate e.g. sodium or potassium carbonate; an alkali metal alkoxide e.g. potassium t-butoxide; butyllitium; or an organic tertiary amine, e.g. triethylamine, or pyridine. Suitable solvents which may be employed in the acylation process include amides e.g. dimethylformamide, or dimethylacetamide; ethers, e.g. tetrahydrofuran or dioxan; halogenated hydrocarbons e.g. methylene chloride; nitriles e.g. acetonitrile and esters e.g. ethyl acetate. The reaction may conveniently be effected at a temperature in the range −10° to +150° C.

Alternatively the acylation may be effected in a two-phase reaction medium, in the presence of a phase transfer catalyst, such as tetrabutylammonium hydrogen sulphate or tetraethylammonium bromide. Thus for example the acylating agent may be reacted with a compound of formula (I) in an inert organic solvent, (e.g. a halogenated hydrocarbon such as methylene chloride), and an aqueous solution of a base (e.g. 50% sodium hydroxide) containing a phase transfer catalyst.

It will be appreciated that in compounds of general formula (I) wherein $R_4$ represents hydrogen, it will be necessary to protect the group $NR_4$ during the acylation process. Suitable protecting groups which may be used include conventional amino protecting groups as described for general process (F) hereinafter.

According to another general process (F), a compound of general formula (I) according to the invention, or a salt thereof may be prepared by subjecting a protected derivative of general formula (I) or a salt thereof to reaction to remove the protecting group or groups.

Thus, at an earlier stage in the preparation of a compound of general formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed.J.F.w. McOmie (Plenum Press 1973) or 'Protective Groups in Organic Synthesis' by Theodora W Greene (John Wiley and Sons 1981).

In compounds of general formula (I) wherein $R_4$ represents hydrogen the group $NR_4$ may be protected for example by protonation or with a conventional amino protecting group. Such groups may include for example arakyl groups, such as benzyl, diphenylmethyl or triphenylmethyl groups; and acyl groups such as N-benzyloxycarbonyl or t-butoxycarbonyl or phthaloyl. The indole nitrogen may also be protected, for example by an aralkyl group such as benzyl. Thus, compounds of general formula (I) wherein one or more of the groups $R_3$ and $R_4$ represents hdyrogen may be prepared by deprotection of a corresponding protected compound.

Removal of any amino protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (for example, by treatment with hydrazine hydrate) or by treatment with a primary amine such as methylamine.

As will be appreciated, in some of the general processes (A) to (E) described above it may be necessary or desired to protect any sensitive groups in the molecule as just described. Thus, a reaction step involving deprotection of a protected derivative of general formula (I) or a salt thereof may be carried out subsequent to any of the above described processes (A) to (E).

Thus, according to a further aspect of the invention, the following reactions may, if necessary and/or desired by carried out in any appropriate sequence subsequent to any of the processes (A) to (E).
(i) removal of any protecting groups; and
(ii) conversion of a compound of general formula (I) or a salt thereof into a physiologically acceptable salt or solvate (for example, hydrate) thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following non-limiting Examples. All temperatures are in 0° C. Solutions were dried with $Na_2SO_4$ unless otherwise indicated. Chromatography was carried out by flash chromatography on silica (Merck 9385) unless otherwise stated.

PREPARATION 1

N-Methyl-1H-indole-5-carboxamide

A mixture of methyl 1H-indole-5-carboxylate (2.5 g) and methylamine in water (33%, 50 ml) was stirred at room temperature for 6 h. The solution was extracted with ethyl acetate (3×50 ml) and the organic extracts were combined and dried. The solvent was removed in vacuo to give an oil which was chromatographed on silica (Kieselgel 60, 100 g) eluting with ethyl acetate to give an oil (1.8 g), which solidifed to give the title compound on standing m.p. 140°–141°.

EXAMPLE 1

3-[1,2,3,6-Tetrahydro-1-(phenylmethyl)pyridin-4-yl]-1H-indole-5-carboxamide maleate A suspension of 1H-indole-5-carboxamide (0.4 g) in galcial acetic acid (20 ml) was heated to 80°under nitrogen, and the resulting solution was treated with aqueous phosphoric acid (2N; 7 ml). Freshly distilled 1-benzyl-4-piperidone (1.4 g) in glacial acetic acid (5 ml) was added and the reaction mixture was stirred at 70° for 18 h, cooled, and poured into a mixture of ice and 0.88 ammonia solution (50 ml) with ice bath cooling. Ethyl acetate (50 ml) was added and the layers were separated. The aqueous layer was extracted with ethyl acetate (4×60 ml), and the combined organic extracts were dried ($MgSO_4$) and evaporated to dryness. The resulting oil was chromatographed on Merck Kieselgel 60 (100 g) eluting with 10% methanol in ethyl acetate. Evaporation of the solvent gave a foam which was treated with maleic acid in methanol/ether to give the title compound as microcrystals (0.19 g), m.p. 164°–166°.

T.l.c. ($SiO_2$) ethylacetate:methanol (9:1) Rf 0.18

The following compounds were similarly prepared by condensation of the appropriate 5-substituted indole with an appropriate piperidone.

a) 3-(1,2,3,6-Tetrahydro-1-methyl-4-pyridinyl)-1H-indole-5-carboxamide as a solid (0.24 g), m.p. 228°-231° after chromatography eluting with methanol.

T.l.c. (SiO$_2$) Ethyl acetate/isopropanol/water/ammonia (50:30:16:4) Rf 0.6.

b) 3-(1,2,3,6-Tetrahydro-1-methyl-4-pyridinyl)-1-methyl-1H-indole-5-carboxamide oxalate as a powder (0.1 g), m.p. 145°-150° after chromatography eluting with dichloromethane/ethanol/0.88 ammonia (100:8:1)

T.l.c. (SiO$_2$) methylene chloride/ethanol/0.88 ammonia (50:8:1) Rf 0.25

EXAMPLE 2

N-Methyl-3-(1,2,3,6-terahydro-1-methyl-4-pyridinyl)-1H-indole-5-carboxamide (i) Methyl 3-(1,2,3,6-tetrahydro-1-methyl-4-pyridinyl)-1H-indole-5-carboxylate Following the method of Example 1, N-methyl-4-piperidone (-0.68 g) and methyl 1H-indole-5-carboxylate (0.5 g) gave the title compound as microcrystals (0.18 g), m.p. 202°-204° following recrystallisation from ethyl acetate.

(ii) N-Methyl-3-(1,2,3,6-tetrahydro-1-methyl-4-pyridinyl)-1H-indole-5-carboxamide A solution of the product of stage (i) (0.5 g) in a mixture of methylamine in ethanol (40%, 20 ml) and methanol (10 ml) was heated at reflux for 10 h. The mixture was cooled, and partitioned between water (100 ml) and ethyl acetate (100 ml). The aqueous phase was separated, and extracted with ethyl acetate (50 ml). The organic layers were combined, dried and evaporated in vacuo to give a solid, (0.25 g) which was crystallized twice from ethyl acetate to give the title compound as microcrystals (0.1 g), m.p. 125°-135°.

T.l.c. (SiO$_2$) Ethyl acetate/isopropanol/0.88 ammonia/water (25:15:8:2) Rf 0.4.

EXAMPLE 3

3-(1,2,3,6-Tetrahydro-4-pyridinyl)-1H-indole-5-carboxamide

A mixture of 1H-indole-5-carboxamide (1.8 g), 4-piperidone hydrochloride monohydrate (3.4 g), and potassium hydroxide (11 g) in methanol (100 ml) was heated at reflux for 16 h. The mixture was cooled, and partitioned between ethyl acetate (200 ml) and saturated potassium carbonate (200 ml). The aqueous phase was separated, and extracted with ethyl acetate (100 ml. The organic extracts were combined, dried and the solvent evaporated in vacuo to give a semi-solid which was triturated with absolute ethanol (10 ml), and washed with ether (3×20 ml). The resultant solid was dried in vacuo to give the title compound, (1.1 g) m.p. 225°-230°.

T.l.c. (SiO$_2$( 0.88 ammonia/methanol (1:24) Rf 0.17

The following compounds were similarly prepared from the appropriate 5-substituted indole by condensation with an appropriate piperidone:

(a) N-Methyl-3-(1,2,3,6-tetrahydro-4-pyridinyl)-1H-indole-5-carboxamide (0.4 g), m.p. 233°-236°.

T.l.c. (SiO$_2$) 0.88 ammonia/methanol (1:24) Rf 0.15

(b) 3-(1,2,3,6-Tetrahydro-1-methyl-4-pyridinyl)-1-H-indole-5-acetamide maleate (0.083 g) m.p. 126°-127°.

T.l.c. (SiO$_2$) Ethyl acetate/isopropanol/water/0.88 ammonia (25:15:8:2) Rf 0.61

(c) 3-(1,2,3,6-Tetrahydro-4-pyridinyl)-1H-indole-5-acetamide maleate (0.18 g), m.p. 180°-181°

T.l.c. (SiO$_2$) Ethyl acetate/isopropanol/water/0.88 ammonia (25:15:8:2) Rf 0.46

(d) 3-(1,2,3,6-Tetrahydro-1-methyl-4-pyridinyl)-1H-indole-5-sulphonamide as a solid (0.3 g) m.p. 190°-200°, after chromatography eluting with ethyl acetate/methanol/ammonia (180:20:1)

Analysis Found: C,57.1; H,6.3; N, 12.4. $C_{14}H_{17}N_3O_2S.O.5C_4H_8O_2$ requires C,57.3; H,6.3; N,12.5%

(e) N,N-Dimethyl-3-(1,2,3,6-tetrahydro-1-methyl-4-pyridinyl)-1H-indole-5-sulphonamide hemihydrate as a solid (0.2 g), m.p. 230°-232°, after flash chromatography eluting with ethyl acetate T.l.c. (SiO$_2$) Methylene chloride/ethanol/0.88 ammonia (50:10:1) Rf 0.35

(f) N-Methyl-3-(1,2,3,6-tetrahydro-1-methyl-4-pyridinyl)-1H-indole-5-methanesulphonamide hydrochloride as a solid (0.77 g), m.p. 120° (decomp), after chromatography eluting with dichloromethane/ethanol/0.88 ammonia (100:8:1)

T.l.c. (SiO$_2$) methylene chloride/ethanol/0.88 ammonia (50:8:1) Rf 0.4

EXAMPLE 4

N-Phenylmethyl-3-(1,2,3,6-tetrahydro-1-methyl-4-pyridinyl)-1H-indole-5-carboxamide hydrochloride hemihydrate (i) N-Phenylmethyl-1H-indole-5-carboxamide Indole-5-carboxylic acid (3.0 g) in anhydrous terahydrofuran (THF) (25 ml) was treated with 1,1-carbonyldiimidazole (CDI) (3.35 g) with stirring at room temperature for 1 h. A further amount (1.0 g) of CDI was added and, after stirring for a further 1H, benzylamine (4.0 g) was introduced. Stirring was continued for 24 h. The solution was diluted with water (50 ml), saturated with sodium chloride, and the THF layer separated off. The organic solution was washed with 1N hydrochloride acid (3×50 ml), brine (2×50 ml), dried (MgSO$_4$) and evaporated under reduced pressure to given an oil (6.0 g) which was chromatographed on silica (Merck 7734, 200 g) eluting with methylene chloride and then methylene chloride/methanol (50:1) to give a foam (4.0 g). Crystallization from ethyl acetate/petroleum/ether (b.p. 60°-80°) gave the title compound as a solid (2.05 g) m.p. 155°-160°.

(ii) N-phenylmethyl-3-(1,2,3,6-Tetrahydro-1-methyl-4-pyridinyl-1H-indole-5-carboxamide hydrochloride hemihydrate A solution of the product of stage (i) (1.0 g) in 2N methanolic potassium hydroxide (64 ml) was treated with distilled N-methyl-4-piperidone (0.47 ml) and heated under reflux for 24 h with stirring. The mixture was concentrated in vacuo to approximately 10 ml and diluted with water (40 ml0. The crude product separated as a solid (1.1 g) and was chromatographed on silica (Merck 7734, 100 g) eluting with methylene chloride/ethanol/0.880 ammonium hydroxide (500:8:1)–(25:8:1) to give a solid (0.3 g). This material was suspended in methanol 925 ml) and treated with excess ethereal hydrogen chloride. The solution was filtered, evaporated to dryness and the residue triturated with anhydrous ether to give the title compound as a powder, (0.38 g) m.p. 279°–282°.

T.l.c. (SiO$_2$) methylene chloride/ethanol/0.88 ammonia (25:8) Rf 0.5

The following compounds were similarly prepared by reacting indole-5-carboxylic acid with an appropriate amine followed by condensation with an appropriate piperidone:

(a) N-Phenylethyl-3-(1,2,3,6-tetrahydro-1-methyl-4-pyridinyl)-1H-indole-5-carboxamide hydrochloride as a foam (0.2 g), T.l.c. S$_1$O$_2$, methylene chloride/ethanol/0.88 ammonia *(50:8:1), Rf 0.45

Analysis Found: C,66.9; H,6.45; N,9.7; C$_{23}$H$_{25}$N$_3$O.HcL.0.82H$_2$O requires C,67.3; H,6.8; N,10.2%

(b) N-(1-Methylethyl)-3-(1,2,3,6-tetrahydro-1-methyl-4-pyridinyl)-1H-indole-5-carboxamide maleate (0.43 g) as a powder, m.p. 175°–180°.

T.l.c. (SiO$_2$) methylene chloride/ethanol/0.88 ammonia (50:8:1) Rf 0.4

(c) N,N-Dimethyl-3-(1,2,3,6-tetrahydro-1-methyl-4-pyridinyl)-1H-indole-5-carboxamide oxalate as a powder (0.06 g), m.p. 141°–146°, after chromatography eluting with methylene chloride/ethanol/ammonia (100:8:1)

T.l.c. (SiO$_2$) ethanol/methylene chloride/0.88 ammonia (100:8:1) Rf 0.3

EXAMPLE 5

N-(1-Methylethyl)-3-(1-Methyl-4-piperidinyl)-1H-indole-5-carboxamide hydrochloride A suspension of 10% palladium oxide on carbon (0.85 g of a 50% paste in water) in ethanol (50 ml) was stirred under hydrogen for 0.5 h. A solution of the free base of the product of Example 4b (0.85 g) in a mixture of 1:1 ethanol-methanol (200 ml) was added to the prereduced catalyst and the mixture stirred under an atmosphere of hydrogen for 4 h. The catalyst was filtered off and the solvent was removed by rotary evaporation to give a foam (0.8 g) which was chromatographed on a column of silica gel (40 g of Merck 7734) eluting with methylene chloride/ethanol/0.88 ammonia (50/8/1) to give the free base of the title compound as a foam (0.7 g). The free base (0.7 g) was dissolved in ethanol (10 ml) and treated with excess ethereal hydrogen chloride. Removal of the solvent, by rotary evaporation, and drying under vacuum at 60° for 18 h gave the title compound as a foam (0.63 g) m.p. 190°–200°.

T.l.c. (SiO$_2$) methylene chloride/ethanol/0.88 ammonia (50:8:1) Rf 0.2

The following compounds were similarly prepared:

(a) N-(2-Phenylethyl)-3-(1-methyl-4-piperidinyl)-1H-indole-5-carboxamide hydrochloride as a foam (0.39 g), m.p. 110°–115°, from the product of Example 4a after chromatography eluting with methylene chloride/ethanol/ammonia.

T.l.c. (SiO$_2$) methylene chloride/ethanol/0.88 ammonia (25:8:1) Rf 0.75

(b) 3-(1-Methyl-4-piperidinyl)-1H-indole-5-carboxamide as a powder (1.09 g), m.p. 118°–120°, from the product of Example 1a in ethanol (30 ml)/water (40 ml).

T.l.c. (SiO$_2$) Ethyl acetate/isopropanol/water/ammonia (25:15:8:2) Rf 0.5

(c) N-Methyl-3-(4-piperidinyl)-1H-indole-5-carboxamide (0.2 g) m.p. 227°–235°, from the product of Example 3a in ethanol and methanol (1:1).

T.l.c. (SiO$_2$) 0.88 ammonia/methanol (1:24) Rf 0.09

(d) 3-(4-Piperidinyl)-1H-indole-5-acetamide, maleate (0.16 g), m.p. 140°–141°, from the product of Example 3c (0.3 g) in methanol.

T.l.c. (SiO$_2$) Ethyl acetate/isopropanol/water/ammonia (25:15:8:2) Rf 0.39

(e) 3-(1-Methyl-4-piperidinyl)-1H-indole-5-acetamide (0.16 g) m.p. 174°–175° from the product of Example 3b (0.3 g) in methanol.

T.l.c. (SiO$_2$) Ethyl acetate/isopropanol/water/ammonium (25:15:8:2) Rf 0.49

(f) 1-Methyl-3-(1-methyl-4-piperidinyl)-1H-indole-5-carboxamide oxalate as a powder (0.53 g), m.p. 200°–205°, from the product of Example 1b in ethanol (100 ml)/dimethylformamide (1 ml) after chromatography eluting with methylene chloride/ethanol/0.88 ammonia (100:8:1)

T.l.c. (SiO$_2$) methylene chloride/ethanol/0.88 ammonia (25:8:1) Rf 0.5

(g) N,N-Dimethyl-3-(1-methyl-4-piperidinyl)-1H-indole-5-carboxamide oxalate as a powder (0.24 g), m.p. 120°–125°, from the free base of the product of Example 4c after chromatography eluting with methylene chloride/ethanol/0.88 ammonia (100:8:1).

T.l.c. (SiO$_2$) methylene chloride/ethanol/0.88 ammonia (75:8:1) Rf 0.75

(h) 3-(1-Methyl-4-piperidinyl)-1H-indole-5-sulphonamide hydrochloride as a solid (0.1 g), m.p. 195°–198°, from the product of Example 3d in methanol.

Analysis Found: C, 51.3; H,7.0; N,10.7. C$_{14}$H$_{19}$N$_2$O$_2$S.HCl.0.5H$_2$O.C$_3$H$_8$O requires C,51.2; H,7.3; N,10.5%.

(i) 3-(1-Methyl-4-piperidinyl)-1H-indole-5-methanesulphonamide hydrochloride as a powder (0.07 g), m.p. 140°–145° (dec.), from the free base of the product of Example 3f after chromatography eluting with methylene chloride/ethanol/0.88 ammonia (100:8:1).

T.l.c. (SiO$_2$) methylene chloride/ethanol/0.88 ammonia (50:8:1) Rf 0.25.

EXAMPLE 6

1-N-Dimethyl-3-(1-methyl-4-piperidinyl)-1H-indole-5-ethanesulphonamide (i) 5-Bromo-3-(1-methyl-4-piperidinyl)-1H-indole A mixture of 5-bromoindole (39.2 g), N-methyl-4-piperidone (25.0 g) and potassium hyroxide pellets (12.0 g) in methanol 9250 ml) was stirred and heated at reflux for 17 h then cooled to 5°, with stirring. The mixture was filtered. The residue was washed consecutively with methanol, water, methanol again and ether and dried in vacuo to give the intermediate tetrahydropyridine (43.3 g) as a powder, with m.p. 256°–261° which was used without further characterisation in the next stage. A solution of ethanolic hydrogen chloride was prepared by adding acetyl chloride (20 ml) to ice-cooled, stirred ethanol (1.31). The intermediate tetrahydropyridine (43.2 g) was dissolved in a portion (0.95 l) of this solution. The hydrochloride salt of the intermediate precipitated out. In order to redissolve this salt the suspension was heated on a steam bath and portions of 2N hydrochloride acid (10 ml), water (15 ml) and con. (11N) hydrochloric acid (10 ml) were added. The resultant solution was added to a prehydrogenated suspension of 5% platinum oxide on carbon (7.0 g) in ethanolic (HCl (0.351 of the above solution) and the mixture was hydrogenated at room temperature and atmospheric pressure until uptake of hydrogen ceased. The mixture was filtered and the solvent was evaporated. The residue was suspended in ethyl acetate (600 ml). Sodium carbonate (2N; 350 ml) was added, with stirring and the mixture was filtered. The residue was washed with water and ethyl acetate and dried in vacuo to give the title compound (33.4 g) as a powder, m.p. 160°–165°.

(ii)
5-Bromo-1-methyl-3-(1-methyl-4-piperidinyl)-1H-indole

The product of stage (i) (2.0 g) was dissolved in dried dimethylformamide (60 ml), and sodium hydride (330 mg dispersion in oil) was added at 5° under nitrogen. After stirring at 5° for 1 h, methyl iodide (0.51 ml) was added at 5°, and the reaction mixture was stirred and warmed to room temperature over 1.5 h. The reaction mixture was treated with 2N Na$_2$CO$_3$ (100 ml), extracted with ethyl acetate (6×50 ml) and the combined organic phases were washed with brine (50 ml), dried (Na$_2$SO$_4$), and evaporated in vacuo to give the title compound as an oil (720 mg) T.l.c. SiO$_2$, CH$_2$Cl$_2$:EtOH:NH$_3$ (100:8:1) Rf 0.1

(iii)
(E)-N-Methyl-2-[1-Methyl-3-(1-methyl-4-piperidinyl)-1H-indole-5-yl]-ethenesulphonamide A mixture of the product of stage (ii) (1.23 g), N-Methylethene sulphonamide (665 mg), triethylamine (1.00 g), tri-o-tolylphosphine (447 mg) and palladium acetate (123 mg) in acetonitrile (9 ml) was stirred and heated at 110° for 16 h in a sealed vessel. The reaction mixture was cooled to room temperature, and the solvent was evaporated to leave a residue. The residue was combined with other impure batches (3.6 g in total) and was purified by 'flash chromatography' (Merck Art, 9385) eluting with CH$_2$Cl$_2$:EtOH:NH$_3$ 100:8:1) to give two impure product was also rechromatographed using the same solvent system to give a foam (120 mg). This was combined with the initial batches of impure product and was rechromatographed by 'flash chromatography' (Merck Art, 9385) eluting with CH$_2$Cl:EtOH:NH$_3$ (200:8:1) to give the product as a foam. Trituration with diethyl ether at 5° gave the title compound as a solid (270 mg) m.p. 155°–159°.

(iv)
1-N-Dimethyl-3-(1-methyl-4-piperidinyl)-1H-indole-5-ethane sulphonamide

A solution of the product of stage (iii) (240 mg) in ethanolic hydrogen chloride (40 ml) was hydrogenated at room temperature and atmospheric pressure over 10% palladium on carbon (50% w/w with H$_2$O, 480 mg) until uptake of hydrogen ceased. The catalyst was filtered and the filtrate was evaporated to leave a residue, which was dissolved in methanol (5 ml) and the solution was basified with 2NNa$_2$CO$_3$ (3 ml). The methanol was evaporated and the residue was partitioned between water (10 ml) and ethyl acetate (100 ml). The aqueous phase was further extracted with ethyl acetate (2×100 ml) and the organic extracts were combined, washed with brine (80 ml) dried (Na$_2$SO$_4$), filtered and evaporated to give an oil. The oil was triturated with diethyl ether (80 ml) at 5° to give the title compound as a solid (144 mg) m.p. 95°–100°.

T.l.c. (SiO$_2$) dichloromethane/ethanol/0.88 ammonia (100:8:1) Rf 0.27

EXAMPLE 7

3-(1-Methyl-4-piperidinyl)-1H-indole-5-propanamide (i) 5-Bromo-3-(1-methyl-4-piperidinyl)-1H-indole A mixture of 5-bromoindole (39.2 g), N-methyl-4-piperidone (25.0 g) and potassium hydroxide pellets (12.0 g) in methanol (9250 ml) was stirred and heated at reflux for 17 h then cooled to 5°, with stirring. The mixture was filtered. The residue was washed consecutively with methanol, water, methanol again and ether and dried in vacuo to give the intermediate tetrahydropyridine (43.3 g) as a powder, with m.p. 256°–261° which was used without further characterisation in the next stage. A solution of ethanolic hydrogen chloride was prepared by adding acetyl chloride (20 ml) to ice cooled, stirred ethanol (1.3l). The intermediate tegrahydropyridine (43.2 g) was dissolved in a portion (0.95 l) of this solution. The hydrochloride salt of the intermediate precipitated out. In order to redissolve this salt the suspension was heated on a steam bath and portions of 2N hydrochloric acid (10 ml), water (15 ml) and conc. (11N) hydrochloric acid (10 ml) were added. The resultant solution was added to a prehydrogenated suspension of 5% platinum oxide on carbon (7.0 g) in ethanolic (HCl (0.351 of the above solution) and the mixture was hydrogenated at room temperature and atmospheric pressure until uptake of hydrogen ceased. The mixture was filtered and the solvent was evaporated. The residue was suspended in ethyl acetate (600 ml). Sodium carbonate (2N; 350 ml) was added, with stirring and the mixture was filtered. The residue was washed with water and ethyl acetate and dried in vacuo to give the title compound (33.4 g) as a powder, m.p. 160°–165°.

(ii)
(E)-3-[3-(1-Methyl-4-piperidinyl)-1H-indol-5-yl]propenamide

A mixture of the product of stage (i) (1.00 g, acrylamide (317 mg) palladium acetate (50 mg), tri-o-tolylphosphine (300 mg) and triethylamine (0.50 ml) in acetonitrile (7 ml) was stirred and heated in a sealed vessel (10 ml) at 100° for 18 h. The supernatant was decanted and evaporated in vacuo to a solid. The tarry residue remaining in the sealed vessel was extracted with hot methanol (10 ml) and the solution combined with the solid obtained above. The mixture was applied to the top of a silica gel column and eluted with a mixture of dichloromethane:ethanol:0.88 ammoni (50:8:1). Evaporation of the solvent in vacuo from the appropriate fractions gave the title compound as an oil (660 mg) which solidified on standing mp 82°–83.5°.

(iii)
3-(1-Methyl-4-piperidinyl)-1H-indole-5-propanamide

A solution of the product of stage (ii) (650 mg) in ethanolic hydrogen chloride was hydrogenated over pre-reduced 10% palladium on carbon (0.20 g of a 50% w/w paste with water) at 25° and atmospheric pressure for 24 h. The catalyst was removed by filtration and the solvent evaporated in vacuo to give a foam. The residue was purified by flash column chromatography eluting with dichloromethane:ethanol:0.88 ammonia (50:8:1). Evaporation of the solvent in vacuo from the appropriate fractions gave the title compound as a foam (188 mg).

T.l.c. SiO$_2$ [CH$_2$Cl$_2$:EtOH:0.88 NH$_3$ 50:8:1] Rf 0.20.
I.r. (CHBr$_3$) NH$_2$ (3520 and 3400) NMe (2785 and 2735) C=O (1678) NH(1588)cm$^{-1}$.

EXAMPLE 8

N-methyl-3(1-methyl-4-piperidinyl)-1H-indole-5-propanamide oxalate (i)
(E)-N-methyl-3-[3-(1-methyl-4-piperidinyl)-1H-indole-5-yl]propaneamide A mixture of 5-bromo-3-(1-methyl-4-piperidinyl)-1H-indole (1.0 g), N-methyl-propenamide (0.38 g), palladium acetate (50 mg), tri-o-tolylphosphine (0.3 g) in a mixture of triethylamine (0.5 ml) and acetonitrile (7 ml) were heated at 100° in a sealed vessel for 24 h. The resulting mixture was evaporated in vacuo and the residue purified by flash chromatography eluting with dichloromethane, ethanol, ammonia (50:8:1) to give the title compound as a solid (1.0 g).

T.l.c. SiO$_2$, CH$_2$Cl$_2$/EtOH/NH$_3$ (50:8:1) Rf 0.3.

(ii)
N-methyl-3-(1-methyl-4-piperidinyl)-1H-indole-5-propanamide oxalate

A solution of the product of stage (i) (1.0 g) in ethanolic hydrogen chloride (100 ml( was hydrogenated over pre-reduced 10% palladium on carbon (50% w/w paste with water, 0.2 g) at room temperature and atmospheric pressure for 17 h. The catalyst was removed by filtration and the cake washed with hot ethanol (50 ml). The combined filtrates were evaporated in vacuo and purified by flash chromatography eluting with a mixture of CH$_2$Cl$_2$/EtOH/NH$_3$ (50:8:1) to give the free base as an oil (0.5 g).

To a stirred solution of the free base (0.5 g) in methylisobutyl ketone (MIBK) (7 ml) at room temperature was added dropwise, a solution of oxalic acid (53.9 mg) in MIBK (3 ml). The resulting suspension was stirred for 5 min, and the solid collected by filtration and washed with MIBK (5 ml). The solid was dried in vacuo at 25° for 6 h end 40° for 2 h to give the title compound as a solid (0.243 g) m.p. 65°-70° (decomp).

T.l.c. SiO$_2$, CH$_2$Cl$_2$/EtOH/NH$_3$ (50:8:1) Rf 0.3.

The following example illustrates a pharmaceutical formulation according to the invention containing a compound of the invention as the active ingredient.

Tablets for Oral Administration

|  | mg/tablet |
|---|---|
| Active Ingredient | 10 |
| Magnesium Stearate BP | 0.5 |
| Anhydrous Lactose | 99 |

The active ingredient is sieved and blended with the anhydrous lactose and magnesium stearate. The mix is then compressed into tablets using a Manasty F$_3$ tablet machine fitted with 8.0 mm concave punches.

Injection for Intravenous Administration

|  | mg/ml |
|---|---|
| Active Ingredient | 0.6 mg |
| Sodium Chloride BP | as required |
| Water for Injection BP | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution was prepared, clarified and filled into appropriate size ampoules sealed by fusion of the glass. The injection is sterilised by heating in an autoclave using one of the acceptable cycles.

Alternatively the solution may be sterilised by filtration and filled into sterile ampoules under aseptic conditions. The solution may be packed under an inert atmosphere of nitrogen or other suitable gas.

We claim:
1. A compound of formula (I)

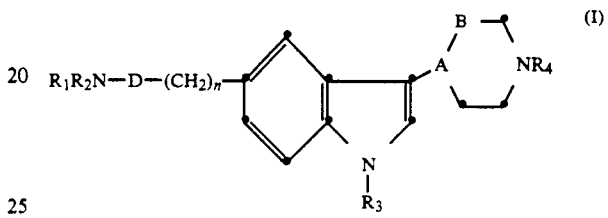

wherein
R$_1$ represents a hydrogen atom, or a C$_{1-6}$ alkyl group;
R$_2$ represents a hydrogen atom, a C$_{1-6}$ alkyl group, a C$_{3-7}$ cycloalkyl group, a C$_{3-6}$ alkenyl group, or a phenyl or phen(C$_{1-3}$) alkyl group in which the phenyl ring is optionally substituted by a halogen atom, a C$_{1-4}$ alkoxy group, a hydroxy group or a C$_{1-3}$ alkyl group;
R$_3$ represents a hydrogen atom, a C$_{1-3}$ alkyl group or a group —CO$_2$R$_5$, —COR$_5$, —COCO$_2$R$_5$ or —CONHR$_5$, where R$_5$ represents a hydrogen atom, a C$_{1-4}$ alkyl group, a C$_{3-7}$ cycloalkyl group, a C$_{2-4}$ alkenyl group or an aryl or ar(C$_{1-4}$)alkyl group in which the aryl group is phenyl which may be unsubstituted or substituted by a halogen atom, a C$_{1-4}$ alkoxy group, a C$_{1-4}$ alkyl group or a hydroxy group, provided that when R$_3$ represents —CO$_2$R$_5$, R$_5$ is other than hydrogen;
R$_4$ represents a hdyrogen atom, a C$_{1-3}$ alkyl group, a C$_{3-6}$ alkenyl group, a phenyl group or a phen(C$_{1-3}$)alkyl group;
A—B represents the group CH—CH$_2$— or C=CH—;
D represents the group —SO$_2$—;
n represents zero or an integer from 1 to 5;
or a pharmaceutically acceptable salt or solvate thereof, provided that when n is 2, R$_3$ is hydrogen and R$_4$ is hydrogen or C$_{1-3}$ alkyl, then R$_2$ is other than hydrogen or C$_{1-6}$ alkyl.

2. A compound according to claim 1, wherein, in the formula (I), A—B represents the group —CH—CH$_2$—.

3. A compound according to claim 1, wherein, in the formula (I), R$_1$ represents a hydrogen atom or a C$_{1-3}$ alkyl group.

4. A compound according to claim 1, wherein, in the formula (I), R$_2$ represents a hydrogen atom or a C$_{1-3}$ alkyl group.

5. A compound according to claim 1, wherein, in the formula (I), R$_1$ and R$_2$ together comprise from 1 to 3 carbon atoms, and when Rand R$_2$ comprise 1 carbon atom, then one of R$_1$ or R$_2$ is hdyrogen.

6. A compound according to claim 1, wherein, in the formula (I), $R_3$ represents a hydrogen atom.

7. A compound according to claim 1, wherein, in the formula (I), $R_4$ represents a $C_{1-3}$ alkyl group.

8. A compound according to claim 1, wherein, in the formula (I), n represents 0, 1 or 2.

9. A compound according to claim 1, wherein in formula (I), n represents 1,2,3,4 or 5.

10. A compound of formula (I)

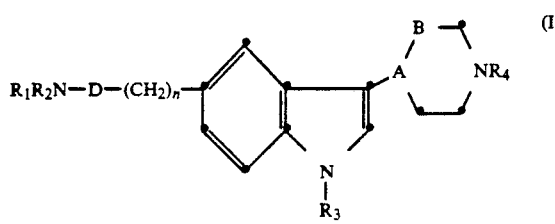

wherein $R_1$ represents a hydrogen atom or a $C_{1-6}$ alkyl group;

$R_2$ represents a hydrogen atom, a $C_{1-6}$ alkyl group, a $C_{3-7}$ cycloalkyl group, a $C_{3-6}$ alkenyl group, or a phenyl or phen($C_{1-3}$) alkyl group in which the phenyl ring is optionally substituted by a halogen atom, a $C_{1-4}$ alkoxy group, a hydroxy group or a $C_{1-3}$ alkyl group;

$R_3$ represents a hydrogen atom, a $C_{1-3}$ alkyl group or a group $-CO_2R_5$, $-COR_5$, $-COCO_2R_5$ or $-CONHR_5$, where $R_5$ represents a hydrogen atom, a $C_{1-4}$ alkyl group, a $C_{3-7}$ cycloalkyl group, a $C_{2-4}$ alkenyl group or an aryl or ar($C_{1-4}$)alkyl group in which the aryl group is phenyl which is phenyl which may be unsubstituted or substituted by a halogen atom, a $C_{1-4}$ alkoxy group, a $C_{1-4}$ alkyl group or a hydroxy group, provided that when $R_3$ represents $-CO_2R_5$, $R_5$ is other than hydrogen;

$R_4$ represents a hydrogen atom, a $C_{1-3}$ alkyl group, a $C_{3-6}$ alkenyl group, a phenyl group or a phen($C_{1-3}$)alkyl group;

A—B represents the group $CH-CH_2-$ or $C=CH-$;

D represents the group $-SO_2-$ or $-CO-$;

n represents the integer from 1 to 5;

or a pharmaceutically acceptable salt or solvate thereof, provided that when n is 2, $R_3$ is hydrogen and $R_4$ is hydrogen or $C_{1-3}$ alkyl, then $R_2$ is other than hydrogen or $C_{1-6}$ alkyl.

11. A compound according to claim 10, wherein in formula (I), D represents the group $-SO_2-$.

12. A compound according to claim 10, wherein in formula (I), D represents the group $-CO-$.

13. A compound according to claim 10, wherein in formula (I), A—B represents the group $-CH-CH_2-$.

14. A compound according to claim 10, wherein in formula (I), $R_1$ represents a hydrogen atom or a $C_{1-3}$ alkyl group.

15. A compound according to claim 10, wherein in formula (I), $R_2$ represents a hydrogen atom or a $C_{1-3}$ alkyl group.

16. A compound according to claim 10, wherein, in the formula (I), $R_1$ and $R_2$ together comprise from 1 to 3 carbon atoms, and when $R_1$ and $R_2$ comprise 1 carbon atom, then one of $R_1$ or $R_2$ is hydrogen.

17. A compound according to claim 9, wherein in formula (I), $R_3$ represents a hydrogen atom.

18. A compound according to claim 9, wherein in formula (I), $R_4$ represents a $C_{1-3}$ alkyl group.

19. A compound according to claim 9, wherein in formula (I), n represents 1 or 2.

20. A compound of formula (Ia)

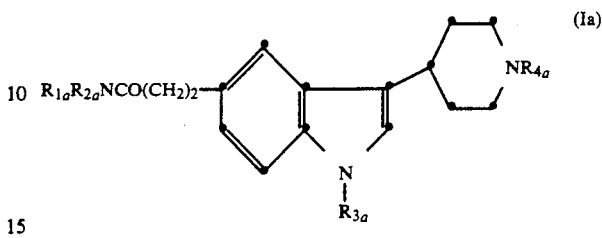

wherein $R_{1a}$ represents a hydrogen atom or a $C_{1-6}$ alkyl group;

$R_{2a}$ represents a hydrogen atom or a $C_{1-6}$ alkyl group;

$R_{3a}$ represents a hydrogen atom or a $C_{1-3}$ alkyl group;

$R_{4a}$ represents a hydrogen atom or a $C_{1-3}$ alkyl group;

or a pharmaceutically acceptable salt or solvate thereof.

21. A pharmaceutical composition for use in the treatment of conditions associated with cephalic pain which comprises an effective amount to treat conditions associated with cephalic pain of at least one compound of formula (I) as defined in claim 1 or a pharmaceutically acceptable salt or solvate thereof together with one or more pharmaceutically acceptable carriers or excipients.

22. A pharmaceutical composition as claimed in claim 21 wherein the conditions associated with cephalic pain are migraine, cluster headache, chronic paroxysmal hemicrania or headache associated with vascular disorders.

23. A pharmaceutical composition as claimed in claim 21 adapted for oral, parenteral or intranasal administration.

24. A method of treating a human susceptible to or suffering from migraine, cluster headache, chronic paroxysmal hemicrania or headache associated with vascular disorder which comprises administering an effective amount of a compound of formula (I)

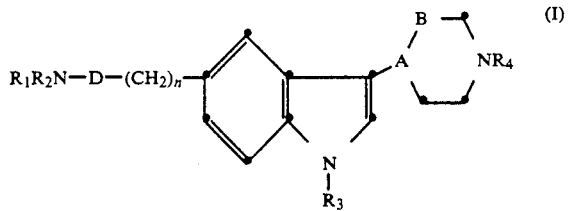

wherein $R_1$ represents a hydrogen atom or a $C_{1-6}$ alkyl group;

$R_2$ represents a hydrogen atom, a $C_{1-6}$ alkyl group, a $C_{3-7}$ cycloalkyl group, a $C_{3-6}$ alkenyl group, or a phenyl or phen($C_{1-3}$)alkyl group in which the phenyl ring is optionally substituted by a halogen atom, a $C_{1-4}$ alkoxy group, a hydroxy group or a $C_{1-3}$ alkyl group;

$R_3$ represents a hydrogen atom, a $c_{1-3}$ alkyl group or a group $-CO_2R_5$, $-COR_5$, $-COCO_2R_5$ or $-CONHR_5$ wherein $R_5$ represents a hydrogen atom, a $C_{1-4}$ alkyl group, a $C_{3-7}$ cycloalkyl group, a $C_{2-4}$ alkenyl group or an aryl or ar($C_{1-4}$)alkyl group in which the aryl group may be unsubstituted or substituted by a halogen atom, a $C_{1-4}$ alkoxy group, a $C_{1-4}$ alkyl group or a hydroxy group (provided that when $R_3$ represents $-CO_2R_5$, $R_5$ is other than hydrogen)

$R_4$ represents a hydrogen atom, a $C_{1-3}$ alkyl group, a $C_{3-6}$ alkenyl group, a phenyl group or a phen($C_{1-3}$)alkyl group;

A—B represents the group $CH-CH_2-$ or $C=CH-$;

D represents the group $-CO-$ or $-SO_2-$;

n represents zero or an integer from 1 to 5;

provided that when D represents the group $-SO_2-$, n is 2, $R_3$ is hydrogen and $R_4$ is hydrogen or $C_{1-3}$ alkyl, then $R_2$ is other than hydrogen or $C_{1-6}$ alkyl; or a pharmaceutically acceptable salt or solvate thereof to said human.

25. A method of treating a human susceptible to or suffering from migraine, cluster headache, chronic paroxysmal hemicrania or headache associated with vascular disorders which comprises administering a pharmaceutical composition according to claim 21.

* * * * *